United States Patent [19]

Singh et al.

[11] Patent Number: 4,578,513
[45] Date of Patent: Mar. 25, 1986

[54] PROCESS FOR PREPARING PHENYLISOPROPYLUREA COMPOUNDS

[75] Inventors: Balwant Singh, Stamford; Paul S. Waterman, Shelton, both of Conn.

[73] Assignee: American Cyanamid Company, Stamford, Conn.

[21] Appl. No.: 672,038

[22] Filed: Nov. 16, 1984

[51] Int. Cl.$^4$ .......................................... C07C 127/17
[52] U.S. Cl. ..................................................... 564/56
[58] Field of Search ...................... 564/56, 54, 53, 52, 564/48

[56] References Cited

U.S. PATENT DOCUMENTS 3,137,697  6/1964  Boswell et al. ....................... 564/48

Primary Examiner—Charles F. Warren
Assistant Examiner—R. A. Picard

[57] ABSTRACT

A new and improved process for making phenylisopropylurea derivatives having the formula:

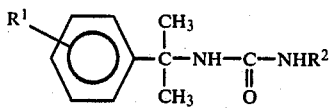

wherein $R^1$ is selected from hydrogen, halogen, alkyl, alkenyl, haloalkyl or $R^2$ groups and $R^2$ is selected from phenyl, alkyl-substituted phenyl alkoxy-substituted phenyl or haloalkyl-substituted phenyl is disclosed. The process comprises reacting a substituted urea of the formula:

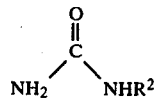

with an alkenyl aromatic compound of the formula:

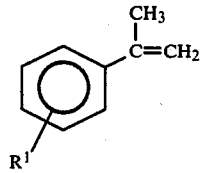

in a polar aprotic solvent, in the presence of an acid catalyst, preferably, sulfuric acid, substituted sulfonic acids or Lewis acids, and stirring the reaction mixture at a temperature of about 20° to 80° C. until formation of the precipitated phenylisopropylurea derivative is substantially complete.

10 Claims, No Drawings

PROCESS FOR PREPARING PHENYLISOPROPYLUREA COMPOUNDS

BACKGROUND OF THE INVENTION

The present invention relates to a process for preparing N-(α,α-dimethylphenyl)urea derivatives. More particularly, it relates to a process for preparing phenylisopropylurea derivatives by the addition of substituted ureas to isopropenyl aromatic compounds.

Phenylisopropylurea derivatives having the general formula:

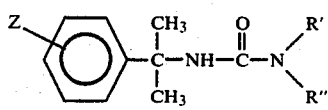

wherein Z is hydrogen, halogen, alkyl or haloalkyl; R' is hydrogen, alkyl, or alkoxy; and R" lower alkyl, substituted alkyl, alkoxy, phenyl or substituted phenyl are presently known and available compounds. The phenylisopropylurea derivatives are known to be potent herbicides, capable of supressing both sprouting of weed seeds and growth of weed seedlings.

These compounds can control such germinating grass weeds as crabgrass (Digitaria sp.), bluegrass (Poa sp.), foxtail (Alopecurus sp.), barnyard grass (Echinochloa sp.), or green foxtail (Setaria sp.), and such broadleaf weeds as lambsquaters (Chenopodium sp.), pigweed (Amaranthus sp.), or chickweed (Stellaria sp.). Especially these compounds are unique in that they exert their action against perennial weeds as nutsedge (Cyperus sp.), sedge (Carex sp.), or spikerus (Eleocharis sp.), which have previously been difficult to control.

The phenylisopropylurea derivatives generally exhibit very low phytotoxicity to such cultivated crop plants as peanuts, cotton and rice, rendering them especially useful and desirable for selectively controlling weeds in growing fields of these particular crops.

The phenyisopropylurea derivatives have been prepared by a variety of methods. In U.S. Pat. No. 3,972,909, for example, N-alkoxy- (or N-alkenyloxy)-N'-(α,α-dimethylbenzyl)-N-phenylureas, useful as selective herbicides, are prepared by reacting N-hydroxy-N'-(α,α-dimethylbenzyl)-N-phenylurea with a $C_1$-$C_4$ haloalkyl or haloalkenyl compound, such as methyl iodide, in the presence of an acid acceptor such as sodium methoxide to form the N-alkoxy or N-alkenyloxy substituted N'-(α,α-dimethylbenzyl)-N-phenylurea in accordance with the equation:

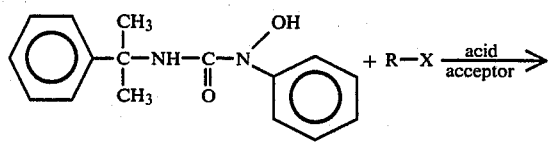

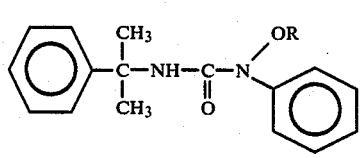

In U.S. Pat. No. 4,039,577 another process for preparing a phenylisopropylurea derivative is disclosed which generally comprises reacting a cumyl halide of the formula:

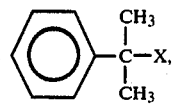

wherein X is halogen, with a urea or urea derivative of the formula:

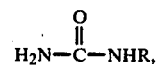

wherein R is hydrogen, phenyl, substituted phenyl, or phenyl alkyl, to form the phenylisopropylurea derivative

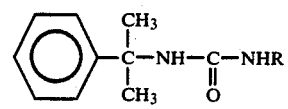

wherein R is the same as defined above. It is also disclosed in said patent that because the cumyl halides are relatively unstable, they may be prepared in situ, by reacting, for example, α-methylstyrene with a hydrogen halide to form the cumyl halide and thereafter adding the urea or urea derivative, or the hydrogen halide may be added to a mixture of α-methylstyrene and the urea or urea derivative, whereby the cumyl halide formed in situ is reacted with the urea compound.

In U.S. Pat. No. 4,078,913, another method is described for preparing 3-(2-phenylisopropyl)urea derivatives which comprises reacting a phenylisopropyl amine compound, which has been prepared by reacting α-methylstyrene with thiocyanic acid to form a phenylisopropylthiocyanate which is further hydrolyzed to form the phenylisopropylamine, and thereafter reacting the amine with either a primary isocyanate compound or an amide chloride to form the 3-(2-phenylisopropyl)urea derivatives in accordance with the following equations:

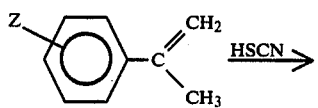

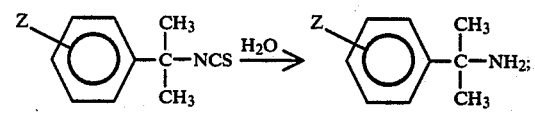

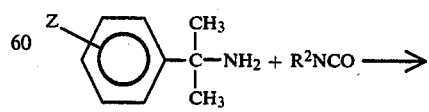

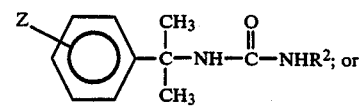

-continued

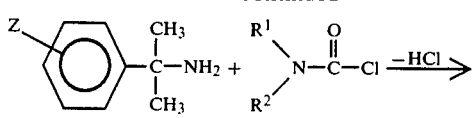

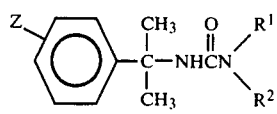

wherein Z is hydrogen or lower alkyl; R is hydrogen or alkyl; and $R^2$ is lower alkyl, phenyl, substituted alkyl or substituted phenyl.

In U.S. Pat. No. 4,143,061 still another process for preparing 3-(α,α-dimethylphenyl)urea compounds of the general formula:

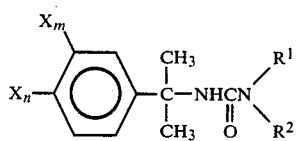

wherein X is halogen or tifluoromethyl, n and m are 0 or 1, $R^1$ is $C_1$–$C_2$ alkyl or $C_1$–$C_2$ alkoxy and $R^2$ is $C_4$–$C_5$ alkyl, cyclohexyl or phenyl, is disclosed which comprises reacting an isocyanate of the formula:

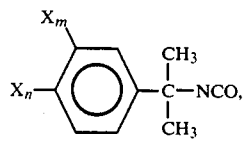

with a secondary amine of the formula:

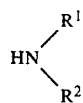

wherein X, m, n, $R^1$ and $R^2$ are as described above.

Each of the above-described methods for preparing phenyisopropyl urea derivatives, although effective to provide useful herbicidal compounds, all require the handling and use of either harmful isocyanates or corrosive halo intermediates which is a serious disadvantage of each of the aforementioned methods.

It has now been discovered that useful herbicidal phenylisopropyl urea derivatives may be prepared without the use of isocyanates or halo intermediates by reacting an alkenyl aromatic compound and urea, or a substituted urea compound, in a polar aprotic solvent in the presence of certain acid catalysts.

SUMMARY OF THE INVENTION

In accordance with the present invention, a new and improved process for preparing phenylisopropylurea derivatives of the formula:

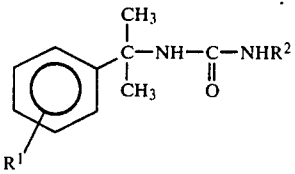

wherein $R^1$ is selected from hydrogen, halogen, alkyl, alkenyl, haloalkyl or $R^2$ groups and $R^2$ is selected from phenyl or alkyl- or alkoxy- or haloalkyl substituted phenyl groups is provided, said process comprising:
(a) providing a reaction mixture comprising:
 (i) a substituted urea of the formula:

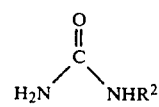

wherein $R^2$ is the same as defined above,
 (ii) a highly polar aprotic solvent; and
 (iii) an effective amount of an acid catalyst, said acid catalyst preferably selected from sulfuric acid, non-mineral acids, and/or Lewis acids;
(b) adding to said reaction mixture an alkenyl aromatic compound of the formula:

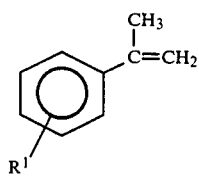

wherein $R^1$ is as defined above; and
(c) stirring the reaction mixture of step (b) at a temperature of from about 20° to about 80° C. until formation of the phenyisopropylurea derivative is substantially complete.

Generally and without limitation, the amounts of acid catalyst used will be from about 0.05 to about 0.2 moles of acid catalyst per mole of urea used. Similarly, the amounts of the alkenyl aromatic compound employed may be from about 1.0 to about 5.0 moles of alkenyl aromatic compound per mole of urea used.

Typically, the reaction is performed at atmospheric pressure, although other pressures may be employed, at a temperature range of between about 20° to about 80° C., preferably 45°–60° C., for a reaction period of from about 5 to about 20 hours, and preferably from about 12 to about 18 hours.

The process of the present invention provides herbicidally active phenylisopropylurea compounds in good yields. The products may be readily isolated by cooling and filtration and can be purified by known procedures such as by washing and recrystallizing in a suitable solvent.

Other advantages of the present invention will become apparent from the following detailed description and illustrative working examples.

DETAILED DESCRIPTION OF THE INVENTION

In accordance with the present invention, phenylisopropylurea derivatives are prepared by first providing a reaction mixture comprising a substituted urea, a solvent and an acid catalyst.

More particularly, the substituted urea compounds for use herein generally comprise substituted ureas of the formula:

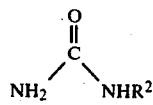

wherein R² is selected from phenyl, alkyl-substituted phenyl, alkoxy-substituted phenyl and haloalkyl substituted phenyl. Suitable substituted ureas for use as starting materials in the present invention include, for example:
1-methylurea;
1-ethylurea;
1-trifluoromethylurea;
1-phenylurea;
1-(2-chlorophenyl)urea;
1-(3-chlorophenyl)urea;
1-(4-chlorophenyl)urea;
1-(o,m- or p-tolyl)urea;
1-(4-isopropylphenyl)urea;
1-(4-ethylphenyl)urea;
1-(2,4-xylyl)urea;
1-(2-methoxyphenyl)urea;
1-(3-methoxyphenyl)urea;
1-(4-methoxyphenyl)urea;
1-(3-trifluoromethylphenyl)urea;
1-(p-diphenyl)urea;
1-(3-chloro-o-tolyl)urea; and
1-(3,4-dichlorophenyl)urea, to name but a few.

The substituted urea compounds are well known commerically available materials or they may be prepared in accordance with known methods, such as for example, by reacting the corresponding amines, such as aniline or toluidine with sodium cyanate in an aqueous solution of hydrochloric acid, as well as by any other known methods.

The reaction mixture of step (a) of the present invention also includes a solvent which is selected from highly polar aprotic solvents. Suitable polar aprotic solvents which can be used include dimethylformamide, acetonitrile, dimethylsulfoxide, nitromethane, nitrobenzene, methylisobutyl ketone, acetone and the like. The highly polar aprotic solvents may be used alone or in further combination with minor amounts of other aprotic solvents such as, for example, dioxane, tetrahydrofuran, cyclohexanone, chloroform, chlorobenzene, benzene, toluene, xylene and diethyl ether, to name but a few. Acetonitrile is the preferred solvent for use in the process of this invention. The amount of solvent employed is generally not critical to this invention.

The reaction mixture in accordance with the present invention also contains a minor effective amount of a certain acid catalyst. More particularly, the acid catalyst for use in the process of this invention is selected from concentrated sulfuric acid, a Lewis acid such as boron trifluoride, aluminum chloride or stannic chloride or a substituted sulfonic acid of the formula R³SO₃H, wherein R³ is selected from alkyl, such as, methyl, ethyl, butyl, etc; haloalkyl, such as trifluoromethyl; phenyl; or alkyl- or haloalkyl-substituted phenyl, such as tolyl, xylyl, trifluoromethylphenyl, and the like. Preferred acid catalysts for use in the process of this invention include chlorosulfonic acid, p-toluenesulfonic acid, trifluoromethylsulfonic acid, boron trifluoride etherate and sulfuric acid.

Generally, the acid catalyst is added in a minor effective amount, and preferably is added in an amount of from about 0.05 to about 0.2 moles of acid catalyst per mole of substituted urea employed.

In accordance with the process of this invention the substituted urea, solvent and acid catalyst are admixed to form a reaction mixture. Thereafter, an alkenyl aromatic compound of the formula:

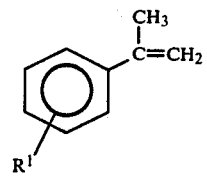

wherein R¹ is selected from hydrogen, halogen, alkyl, alkenyl, or haloalkyl R² groups is added. Illustrative of the alkenyl aromatic compounds for use herein are: α-methylstyrene, o-,m- and p-isopropyltoluene; m- and p-trifluoromethylisopropenylbenzene; o-m-, p-chloroisopropenylbenzene; m- and -p-diisopropenylbenzene, and the like. The preferred alkenyl aromatic compound for use herein is α-methylstyrene.

Generally, the reaction in accordance with this invention proceeds almost stoichiometrically, however from the standpoint of inhibiting any side reactions or improving economy and productivity, the reaction is carried out preferably by using either one of the starting materials in a slight excess. Generally, it is preferable to employ an excess of the alkenyl aromatic compound and generally the alkenyl aromatic compound will be added to the reaction mixture of this invention in amounts of between about 1.0 to about 5 moles of alkenyl aromatic compound per mole of substituted urea.

In accordance with the method of the present invention, the alkenyl aromatic compound is added to the reaction mixture comprising substituted urea, solvent and acid catalyst, and the resulting mixture is stirred at a temperature of from about 20° to about 80° C. and preferably about 45° about 65° C. for a time sufficient to allow the reaction to proceed until substantially complete. Typically, the reaction mixture will be heated and stirred for a period of from about 5 to about 20 hours, preferably for about 12 to 18 hours until precipitate formation is substantially complete.

Thereafter, the precipitated phenylisopropylurea derivative may be collected by filtration.

The phenylisopropylurea derivatives may be purified, if desired, by washing the precipitate with a hydrocarbon solvent, such as hexane, or other suitable solvent, followed by recrystallization in a suitable solvent such as methylene chloride or toluene.

In order that those skilled in this art may better understand how the present invention may be practiced, the following working examples are provided by way of illustration and not by way of limitation.

DESCRIPTION OF THE PREFERRED EMBODIMENTS

EXAMPLE 1

A phenylisopropylurea derivative was prepared as follows:

A reaction mixture was prepared by mixing 7.8 parts by weight of acetonitrile at 45° C. with 0.04 parts by weight of N-(p-tolyl)urea and 0.07 parts by weight of chlorosulfonic acid. After one minute, 3 parts of α-methylstyrene were added and the reactants were stirred at 55° C. for 18 hours.

The reaction mixture was then allowed to cool to room temperature and was filtered to collect the precipitate. The precipitated solid was washed with hexane and thereafter was recrystallized from methylene chloride to yield 0.7 parts by weight of N-(α,α-dimethylbenzyl)-N'-(p-tolyl)urea having a melting range of about 199° to 200° C.

EXAMPLE 2

A phenylisopropylurea derivative was prepared in accordance with the method of Example 1, as follows: 1.5 parts of N-(p-tolyl)urea was suspended in 3.93 parts of acetonitrile at 55°, and 0.3 parts of p-toluene-sulfonic acid was added. After 1 minute, 4.7 parts of α-methylstyrene were added. The reactants were stirred at 55° C. for 18 hours. After cooling to ambient temperature, 60 parts of hexane was added and the precipitated solid collected, washed with hexane and recrystallized from methylene chloride to afford 2.2 parts of N-(α,α,-dimethylbenzyl)-N'-(p-tolyl)urea.

EXAMPLE 3

The same procedure as in Example 2 was repeated except that 0.22 parts of trifluoromethylsulfonic acid was used instead of p-toluenesulfonic acid. There was obtained 1.2 parts of N-(α,α-dimethylbenzyl)-N'-(p-tolyl) urea.

EXAMPLE 4

The same procedure as in Example 2 was repeated except that 0.6 parts of a 1.32N toluene solution of dodecylbenzenesulfonic acid was used instead of p-toluenesulfonic acid. There was obtained 2.2 parts of N-(α,α-dimethylbenzyl)-N'-(p-tolyl)urea.

EXAMPLE 5

The same procedure as in Example 2 was repeated except that 0.23 parts of boron trifluoride etherate was used instead of p-toluenesulfonic acid. There was obtained 1.75 parts of N-(α,α-dimethylbenzyl)-N'-(p-tolyl)urea.

EXAMPLE 6

The same procedure as in Example 2 was repeated except that 0.11 parts of sulfuric acid (98%) was used instead of p-toluenesulfonic acid. There was obtained 1.2 parts of N-(α,α-dimethylbenzyl)-N'-(p-tolyl)urea.

EXAMPLE 7

The same procedure as in Example 2 was repeated except 3.16 parts of m-diisopropenylbenzene was used instead of α-methylstyrene. There was obtained 2.2 parts of N-(α,α-dimethyl-m-isopropenylbenzyl)-N'-(p-tolyl)urea (N-2-(m-isopropenylphenyl)isopropyl N'-(p-tolyl)urea).

EXAMPLE 8

The same procedure as in Example 2 was repeated except 2 parts of p-diisopropenylbenzene was used instead of α-methylstyrene. There was obtained 1.2 parts of N-2-(p-isopropenylphenyl)isopropyl-N'-(p-tolyl)urea.

The new and improved process of the present invention provides a method for making useful phenylisopropylurea derivatives in good yield without using harmful isocyanates or corrosive halo intermediates.

The foregoing patents are incorporated herein by reference. Although the present invention has been described with reference to certain preferred embodiments, it is apparent that modifications or changes may be made therein by those skilled in this art, without departing from the scope and spirit of the present invention as defined by the appended claims.

What is claimed is:

1. A process for preparing phenylisopropyl urea derivatives of the formula:

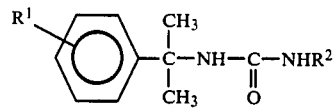

wherein $R^1$ is selected from hydrogen, alkyl, alkenyl, halogen, haloalkyl or $R^2$ and $R^2$ is selected from phenyl or alkyl-, alkoxy- or haloalkyl-substituted phenyl, said process comprising:
(a) providing a reaction mixture comprising:
(i) a substituted urea of the formula

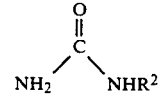

wherein $R^2$ is the same as defined above;
(ii) a highly polar aprotic solvent; and
(iii) an effective amount of an acid catalyst;
(b) thereafter, adding an alkenyl aromatic compound of the formula:

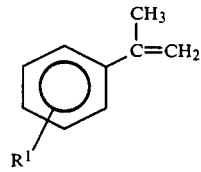

wherein $R^1$ is the same as described above; and
(c) stirring the reaction mixture of step (b) at a temperature of from about 20° to about 80° C. until formation of the phenylisopropylurea derivative is substantially complete.

2. A process as recited in claim 1 wherein the substituted urea is N-(p-tolyl)urea.

3. A process as recited in claim 1, wherein the alkenyl aromatic compound is α-methylstyrene.

4. A process as recited in claim 1, wherein the alkenyl aromatic compound employed is m- or p-diisopropenylbenzene.

5. A process as recited in claim 1, wherein the highly polar aprotic solvent is selected from the group consisting of dimethylformamide, acetonitrile, dimethylsulfoxide, nitromethane, nitrobenzene, methylisobutyl ketone, acetone and mixtures of any of the foregoing aprotic solvents, alone or in further combination with other aprotic solvents selected from the group consisting of dioxane, tetrahydrofuran, cyclohexanone, chloroform, chlorobenzene, benzene, toluene, xylene, diethyl ether and mixtures of any of the foregoing.

6. A process as recited in claim 1, wherein the acid catalyst is selected from Lewis acids selected from the group consisting of boron trifluoride, aluminum chloride, and stannic chloride, or substituted sulfonic acids of the formula $R^3HSO_3$, wherein $R^3$ is alkyl, haloalkyl, phenyl, or alkyl- or haloalkyl-substituted phenyl.

7. A process as recited in claim 1, wherein the alkenyl aromatic compound is added in an amount of from about 1.0 to about 5.0 moles of alkenyl aromatic compound per mole of substituted urea.

8. A process as recited in claim 1, wherein the acid catalyst is added in an amount of from about 0.05 to about 0.2 moles per mole of substituted urea.

9. A process as recited in claim 1, further comprising the steps of:
(d) cooling the reaction mixture of step (c) to about room temperature and filtering any precipitated solids.

10. A process as recited in claim 9, further comprising the steps of washing the precipitated solids and recrystallizing the solids in a suitable solvent to obtain a purified phenylisopropylurea derivative product.

* * * * *